United States Patent [19]

Petrov et al.

[11] Patent Number: 5,654,467

[45] Date of Patent: Aug. 5, 1997

[54] PROCESS FOR THE PRODUCTION OF C-SUBSTITUTED DIETHYLENETRIAMINES

[75] Inventors: Orlin Petrov; Jean-Claude Hilscher; Klaus Nickisch; Heribert Schmitt-Willich; Heinz Gries; Bernd Radüchel; Johannes Platzek, all of Berlin, Germany

[73] Assignee: Schering Aktiengesellschaft, Berlin, Germany

[21] Appl. No.: 495,474

[22] PCT Filed: Jan. 8, 1994

[86] PCT No.: PCT/EP94/00034

§ 371 Date: Oct. 12, 1995

§ 102(e) Date: Oct. 12, 1995

[87] PCT Pub. No.: WO94/17033

PCT Pub. Date: Aug. 4, 1994

[30] Foreign Application Priority Data

Jan. 25, 1993 [DE] Germany ............... 43 02 289.8

[51] Int. Cl.$^6$ ............... C07C 269/06; C07C 271/20
[52] U.S. Cl. ............... 560/29; 560/32; 560/115; 560/159; 561/368; 561/369; 561/447; 561/468; 561/478; 561/512
[58] Field of Search ............... 560/29, 32, 115, 560/159; 564/368, 369, 447, 478, 468, 512

[56] References Cited

U.S. PATENT DOCUMENTS 2,364,178  12/1944  Wilson ............... 564/468
3,236,895  2/1966  Lee et al. ............... 564/505

FOREIGN PATENT DOCUMENTS 405704     1/1991   European Pat. Off. .
466200     1/1992   European Pat. Off. .
1155122    10/1963  Germany .
WO91/14459 10/1991  WIPO .

*Primary Examiner*—Richard L. Raymond
*Attorney, Agent, or Firm*—Millen, White, Zelano, & Branigan, P.C.

[57] ABSTRACT

The invention relates to a process for the production of C-substituted diethylenetriamines of general formula

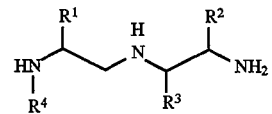

in which $R^1$, $R^2$, $R^3$ and $R^4$ have different meanings.

6 Claims, No Drawings

PROCESS FOR THE PRODUCTION OF C-SUBSTITUTED DIETHYLENETRIAMINES

This application is a 371 of PCT/EP94/00034, filed Jan. 8, 1994.

The invention relates to the object characterized in the claims, i.e., a process for the production of C-substituted diethylenetriamines.

In the literature, various processes to synthesize C-substituted diethylenetriamines are described, which all proceed according to the same basic system [see, e.g., Inorganic Chem. 25 (1986) 2772; DE 37 10 730; U.S. Pat. No. 4,622,420; Nucl. Med. Biol. (1991) 313; WO 91/14459]. In this connection, an amino acid ester with a free or protected amino group is reacted with ethylenediamine to the corresponding amide. Then, the amide is reduced with diborane to amine, and optionally present protective groups can be cleaved beforehand.

This method is subject to the following drawbacks:

a) A large borane excess (5–10 molar equivalents) is necessary, since the amide to be reduced is secondary and still contains two free amino groups.

b) The intermediate stages are poorly crystallizable and difficult to purify.

c) Because of the toxicity and the high price of the borane, this process is not suitable for use on an industrial scale or is at least economically unprofitable because of the high safety expense to be borne.

d) Very long reaction times as well as high reaction temperatures are necessary (18–30 hours in the boiling heat).

Attempts to replace the diborane by other, more easily manageable reducing agents, such as, e.g., lithium aluminum hydride (LAH) or diisobutylaluminum hydride (DIBAH), came to nothing. Complex reaction mixtures thus result in the case of LAH. But DIBAH cannot be used universally either, thus, e.g., phenolether groups optionally contained in the molecule (as C-substituent) are cleaved.

Therefore, there still exists a great interest in a technically feasible, universally applicable process for the production of C-substituted diethylenetriamines, all the more so as said substances are important feedstocks for the production of derivatized diethylenetriaminepentaacetic acids, which just as the diethylenetriamines themselves are an important family of substances in the pharmaceutical industry [see, e.g., U.S. Pat. No. 4,622,420; Inorg. Chem. 25 (1986) 2772; EP 0 405 704; Nucl. Mol. Biol. (1991) 31 ].

Thus, especially metal complexes of the pentaacetic acid derivatives are important compounds for the production of contrast media in the field of diagnosis (EP 0 405 704).

The object of the invention is therefore to provide a generally applicable process for the production of C-substituted diethylenetriamines that surmounts the drawbacks of the prior art and especially manages without the use of the expensive and toxic diborane.

This object is achieved by the process, according to the invention, for the production of carbon-substituted diethylenetriamines of general formula I

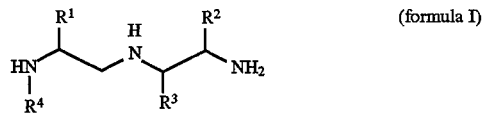

(formula I)

in which $R^1$ stands for a group $-(CH_2)_m-(C_6H_4)_q-(O)_k-(CH_2)_n-(C_6H_4)_r-(O)_r-R$ or for a group $-(CH_2)_m-(C_6H_{10})_q-(O)_k-(CH_2)_n-(C_6H_{10})_r-(O)_r-R$, in which m and n, independently of one another, mean numbers 0–5, k, l, q and r, independently of one another, mean numbers 0 or 1, R stands for a hydrogen atom, a protective group, an optionally $OR^5$-substituted $C_1-C_6$ alkyl radical or a $CH_2-COOR^5$ group, with $R^5$ meaning a hydrogen atom, a $C_1-C_6$ alkyl radical or a benzyl group, provided that a direct oxygen-oxygen bond is not allowed, $R^2$ and $R^3$ each stand for a hydrogen atom or together form a $-(CH_2)_p-$alkylene bridge, in which p means numbers 3 or 4 and $R^4$ stands for an amino protective group, preferably for a benzyloxycarbonyl group, which is characterized in that an aminoethylalcohol, protected on the nitrogen, of general formula II

(formula II)

in which $R^1$ and $R^4$ have the indicated meanings, is reacted with methanesulfonic acid chloride, tosyl chloride or trifluoroacetic anhydride in an organic solvent, by adding a base, to the corresponding mesylate, tosylate or triflate, is then filtered and the filtrate is reacted with an ethylenediamine of general formula III

(formula III)

in which $R^2$ and $R^3$ have the indicated meanings to the desired nitrogen-protected, carbon-substituted triamine of general formula I.

The process according to the invention thus starts from easily accessible nitrogen-protected aminoethyl alcohols, which are first reacted with methanesulfonic acid chloride, toluenesulfonic acid chloride or trifluoroacetic anhydride in a nonprotic organic solvent, such as, e.g., THF, diethyl ether or dioxane by adding a base, preferably triethylamine. In this connection, in addition to the 2-aminoethanol-alcohol groups, also other OH groups, optionally containing $R^1$ in the radical, are converted to the corresponding mesylate, tosylate or triflate. The latter can optionally be cleaved again in a later reaction step according to methods known to one skilled in the art or, if desired, converted.

The thus obtained mesylates, tosylates or triflates are reacted directly with ethylenediamine, 1,2-diaminocyclopentane or 1,2-diaminocyclohexane to the corresponding monoprotected triamines. A previous isolation or purification of the mesylates (tosylates, triflates) is not necessary in this case.

The N-protected aminoethyl alcohols of general formula II, required as initial substances, are easily accessible in the way known to one skilled in the art [Bull. Chem. Soc. Japan (1984) 2327] by reduction of an N-protected amino acid ester of general formula IV

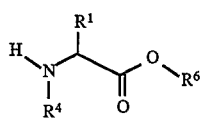
(formula IV)

in which
R¹ and R⁴ have the indicated meanings and
R⁶ stands for a straight-chain or branched $C_1$–$C_6$ alkyl radical with $NaBH_4$ in an organic solvent.

Instead of $NaBH_4$, $LiBH_4$ (J. Org. Chem. (1982) 1604] or $NaBH_4$ with an addition of LiBr (Tetrahedron Letters (1988) 4919] can also be used as reducing agents.

If desired, the nitrogen protective group of the carbon-substituted diethylenetriamines of general formula I can be cleaved in the way known to one skilled in the art (T. Green "Protective Groups in Organic Synthesis," Wiley (1981) 239). Suitably, the carbon-substituted diethylenetriamines of general formula I are purified in it by acidification with hydrochloric acid and conversion to the corresponding hydrochlorides. The latter are then recrystallized from a suitable organic solvent, such as, e.g., alcohols, preferably methanol. Then, amino protective group $R^4$ is hydrogenated off by using a suitable Pd catalyst. As reaction media, alcohols are also suitable. After completion of the hydrogenolysis, the catalyst is filtered off and then the salt is crystallized out from the filtrate.

The amine can optionally be released from the crystallizate (hydrochloride) by adding an inorganic base, preferably NaOH.

The process according to the invention avoids the use of the toxic diborane, the product can be obtained in high purity and yield because of the good crystallization behavior of the intermediate stages. Thus, the alkylation of the diamines with the corresponding mesylates, tosylates or triflates proceeds not only in better yield than in the conventional synthesis (borane reduction), but also in better yield and higher selectivity than in the already previously known monoalkylation of ethylenediamine with single alkyl halides, as is described, e.g., in J. Am. Chem. Soc. 67 (1945) 1531 or in EP 0 466 200.

Because of the fundamental differences of the process according to the invention and the process with borane reduction, a yield comparison is useful and possible only with the entire method of synthesis, e.g., relative to the same initial and end products.

Thus, for the synthesis of (S)-1-(4-ethoxybenzyldiethylenetriamine) from the (S)-N-benzyloxycarbonyl-O-ethyltyrosine methyl ester in the process according to the invention, over 80% of the total yield is achieved (Examples 1a–d), while in the process with the corresponding amide, followed by the cleavage of the benzyloxycarbonyl radical and a reduction with diborane, the total yield is only approximately 60%.

The invention is explained by the following examples, without intending it to be limited to the latter.

EXAMPLE 1 a) N-Benzyloxycarbonyl-O-ethyltyrosine methyl ester 32.94 g (100 mmol) of N-benzyloxycarbonyltyrosine methyl ester is mixed in 200 ml of DMF with 27.64 g (200 mmol) of ground potassium carbonate. 8.96 ml (110 mmol) of iodoethane is instilled in this suspension and stirred overnight at room temperature. The solution is concentrated by evaporation, distributed between ethyl acetate and water and, after drying ($Na_2SO_4$), the organic phase is mixed with hexane. The title compound crystallizes out.

Yield: 32.88 g (92%)
Melting point: 50°–56° C.
Analysis: Cld: C 67.21 H 6.49 N 3.92 Fnd: C 66.96 H 6.57 N 3.81 b) (S)-N-Benzyloxycarbonyl-2-(4-ethoxybenzyl)-2-aminoethanol 31.80 g (848.4 mmol) of sodium borohydride is added to a solution of 221.41 g (605.9 mmol) of (S)-N-benzyloxycarbonyl-O-ethyltyrosine methyl ester in 1.5 l of tetrahydrofuran at room temperature. 270 ml of methanol is instilled in it with stirring within 2 hours. Then, the tetrahydrofuran is distilled off in a vacuum, the residue is taken up in 1 l of water and extracted three times with 700 ml of ethyl acetate. The combined organic phase is washed with water, dried with sodium sulfate and concentrated. It is recrystallized from ethyl acetate/hexane.

Yield: 187.0 g (93.7%)
Melting point: 112°–117° C.
Analysis: Cld: C 69.28 H 7.04 N 4.25 Fnd: C 68.93 H 7.27 N 3.96 c) (S)-N-Benzyloxycarbonyl-N'-(2-aminoethyl)-1-(4-ethoxybenzyl)ethylenediamine 20.86 ml (267.8 mmol) of methanesulfonyl chloride is slowly instilled in a solution of 84.00 g (255.0 mmol) of (S)-N-benzyloxycarbonyl-2-(4-ethoxybenzyl)-2-aminopropanol and 37.82 ml (272.9 mmol) of triethylamine in 330 ml of tetrahydrofuran at 4° C. with stirring. After 2 hours, the settled precipitate is filtered off and the filtrate is mixed with 427.0 ml (6.4 mol) of ethylenediamine. The solution is stirred for 4 hours at 50° C. and then concentrated in a vacuum. The residue is taken up with water, extracted with ethyl acetate, dried with sodium sulfate and concentrated on a rotary evaporator. The residue is taken up in methanol and acidified at 0° C. with concentrated hydrochloric acid. After suctioning off and drying, the product is obtained in the form of colorless crystals as dihydrochloride.

Yield: 95.7 g (84.5%)
Melting point: 223°–225° C. (dec.)
Analysis: Cld: C 56.76 H 7.03 N 9.46 Cl 15.96 Fnd: C 55.34 H 6.94 N 9.45 Cl 16.32

¹H-NMR (CDCl₃, free base): 7.45–7.29 m [5]; 7.15 d, J=8 Hz, [2]; 6.80 d, J=8 Hz, [2]; 5.25 br. d [1]; 5.08 ABq [2]; 3.98 q, J=6 Hz, [2]; 3.90 m [1]; 2.90–2.55 m [8]; 1.50 br. s [3]; 1.40 tr, J=6 Hz [3 ].

d) (S)-1-(4-Ethoxybenzyl)diethylenetriamine 90.0 g (202.5 mmol) of (S)-N-benzyloxycarbonyl-N'-(2-aminoethyl)-1-(4-ethoxybenzyl)-ethylenediamine dihydrochloride is suspended in 2.7 l of methanol, and, after adding 7.5 g of 10% Pd/C, hydrogenated for 1 hour at 15 bars. Then, the catalyst is filtered off and the filtrate is concentrated to 150 ml. The precipitated crystals are suctioned off.

Yield: 56.86 g (90.5%)
Melting point: 227°–231° C. (dec.)
Analysis: Cld: C 50.33 H 8.12 N 13.54 Cl 22.85 Fnd: C 50.71 H 8.32 N 13.77 Cl 23.27

To release the triamine, 14.7 g (366 mmol) of pulverized NaOH is added to a suspension of the thus obtained crystals in 100 ml of methanol. The precipitated sodium chloride is filtered off and the filtrate is concentrated by evaporation. After drying at 50° C. in a vacuum, 43.5 g (100%) of a colorless oil is obtained.

EXAMPLE 2 a) (S)-N-Benzyloxycarbonyl-3-(4-hydroxybenzyl)-2-aminopropanol 15.75 g (400 mmol) of sodium borohydride is added to a solution of 50.0 g (151 mmol) of (S)-N- benzyloxycarbonyltyrosine methyl ester in 0.5 l of tetrahydrofuran at room temperature. 100 ml of methanol is instilled in it with stirring within 2 hours. The reaction mixture is stirred for 2 hours at 50° C. Then, the tetrahydrofuran is distilled off in a vacuum, the residue is taken up in 400 ml of water and extracted three times with 300 ml of ethyl acetate each. The combined organic phases are washed with water, dried with sodium sulfate and concentrated. It is recrystallized from ethyl acetate/hexane.

Yield: 41.5 g (91%)

Melting point: 79°–82.5° C.

Analysis: Cld: C 67.76 H 6.36 N 4.65 Fnd: C 68.12 H 6.37 N 4.73 b) (S)-N-Benzyloxycarbonyl-N'-(2-aminoethyl)-1-(4-methylsulfonyloxybenzyl)-ethylenediamine 7.14 g (60.6 mmol) of methanesulfonyl chloride is slowly instilled in a solution of 7.3 g (24.2 mmol) of (S)-N-benzyloxycarbonyl-2-(4-hydroxybenzyl)-2-aminopropanol and 7.35 g (72.7 mmol) of triethylamine in 30 ml of tetrahydrofuran at 4° C. with stirring. After 2 hours, the settled precipitate is filtered off and the filtrate is mixed with 29.1 g (484 mmol) of ethylenediamine. The solution is stirred for 4 hours at 50° C. and then concentrated in a vacuum. The residue is taken up in water, extracted with ethyl acetate, dried with sodium sulfate and concentrated on a rotary evaporator. The residue is taken up in methanol and acidified at 0° C. with concentrated hydrochloric acid. After suctioning off and drying, the product is obtained in the form of colorless crystals as dihydrochloride.

Yield: 9.4 g (79%)

Melting point: 216°–218° C. (dec.)

Analysis: Cld: C 48.58 H 5.91 N 8.50 Cl 14.34 Fnd: C 48.71 H 6.32 N 8.74 Cl 13.97

$^1$H-NMR (CDCl$_3$, free base): 7.4–7.15 m [9]; 5.2 br, d, J=9 Hz, [1]; 5.08 s [2]; 3.94 m [1]; 3.14 s [3]; 2.95–2.60 m [8]; 1.52 br. s [3].

c) (S)-1-(4-Methylsulfonyloxybenzyl)diethylenetriamine 5.0 g (10.1 mmol) of (S)-N-benzyloxycarbonyl-N'-(2-aminoethyl)-1-(4-methylsulfonyloxybenzyl) ethylenediamine dihydrochloride is suspended in 50 ml of methanol and, after adding 0.84 g of 10% Pd/C catalyst, hydrogenated for 4 hours at 15 bars. Then, the catalyst is filtered off, the filtrate is mixed with 1 ml of concentrated hydrochloric acid and concentrated by evaporation to 20 ml. The precipitated crystals are suctioned off.

Yield: 3.6 g (90%)

Melting point: 226°–230° C.

Analysis: Cld: C 36.33 H 6.10 N 10.59 Cl 26.81 Fnd: C 36.71 H 6.32 N 10.73 Cl 26.27

To release the triamine, 1.1 g (27.3 mmol) of pulverized sodium hydroxide is added to a suspension of the thus obtained crystals in 10 ml of methanol. The precipitated sodium chloride is filtered off and the filtrate is concentrated by evaporation. After drying at 50° C. in a vacuum, 2.6 g (100%) of a colorless oil is obtained.

EXAMPLE 3

N-(2-Benzyloxycarbonylamino-3-phenylpropyl)-cyclopentyl-1,2-diaminodihydrochloride 1.64 ml (21 mmol) of methanesulfonyl chloride is slowly instilled in a solution of 5.7 g (20 mmol) of N-benzyloxycarbonyl-phenylalaninol [Correa et al. Synth. Commun. 21, 1–9 (1991)] and 3.0 ml (21.7 mmol) of triethylamine in 30 ml of tetrahydrofuran at 4° C. with stirring. After 2 hours, the settled precipitate is filtered off and the filtrate is instilled in 50.1 g (500 mmol) of 1,2-diaminocyclopentane [Jaeger and Blumendal], Z. anorg. Chem. 175, 161 (1928)]. The solution is stirred for 4 hours at 50° C. and then concentrated in a vacuum. The residue is taken up with water, extracted with ethyl acetate, dried with sodium sulfate and concentrated by evaporation on a rotary evaporator. The remaining oil is taken up in methanol and acidified at 0° C. with concentrated hydrochloric acid. After suctioning off and drying, the product is obtained in amorphous form.

Yield: 7.1 g (81%)

Analysis: Fnd: C 60.00 H 7.09 Cl 16.10 N 9.54 Cld: C 59.43 H 7.20 Cl 16.61 N 9.29

EXAMPLE 4

N-(2-Benzyloxycarbonylamino-4-methylpentyl)-cyclohexyl-1,2-diaminodihydrochloride 1.64 ml (21 mmol) of methanesulfonyl chloride is slowly instilled in a solution of 5.0 g (20 mmol) of N-benzyloxycarbonyl-leucinol [Correa et al. Synth. Commun. 21, 1–9 (1991)] and 3.0 ml (21.7 mmol) of triethylamine in 30 ml of tetrahydrofuran at 4° C. with stirring. After 2 hours, the settled precipitate is filtered off and the filtrate is instilled in 120 ml (1 mol) of trans-1,2-diaminocyclohexane. The solution is stirred for 4 hours at 50° C. and then concentrated in a vacuum. The residue is taken up with water, extracted with ethyl acetate, dried with sodium sulfate and concentrated by evaporation on a rotary evaporator. The remaining oil is taken up in methanol and acidified at 0° C. with concentrated hydrochloric acid. After suctioning off and drying, the product is obtained in amorphous form.

Yield: 7.1 g (84%)

Analysis: Cld: C 57.14 H 8.39 Cl 16.87 N 9.99 Fnd: C 57.43 H 8.20 Cl 16.22 N 9.69

EXAMPLE 5 a) N-Benzyloxycarbonyl-O-methyl-tyrosine methyl ester 32.94 g (100 mmol) of N-benzyloxycarbonyl-tyrosine methyl ester is mixed in 200 ml of DMF with 27.64 g (200 mmol) of ground potassium carbonate. 15.6 g (110 mmol) of iodomethane is instilled in this suspension and stirred overnight at room temperature. The solution is concentrated by evaporation, distributed between ethyl acetate and water, and, after drying (Na$_2$SO$_4$), the organic phase is mixed with hexane. The title compound crystallizes out.

Yield: 31.9 g (93%)

Analysis: Cld: C 66.46 H 6.16 N 4.08 Fnd: C 66.60 H 6.23 N 3.99 b) N$_a$-Benzyloxycarbonyl-O-methyl-tyrosine-(2-aminocyclohexy)-amide-hydrochloride 24.0 g (70 mmol) of N-benzyloxycarbonyl-O-methyl-tyrosine methyl ester is dissolved in 50 ml of methanol and instilled in about 2 hours in 420 ml (3.5 mol) of trans-1,2-diaminocyclohexane. The solution is stirred for 24 hours at room temperature and then evaporated to dryness in an oil vacuum. The oily residue is taken up in ethyl acetate and shaken out several times to remove diaminocyclohexane residues with water. The organic phase is dried (Na$_2$SO$_4$) and mixed with 2N hydrogen chloride in ethyl acetate. The precipitate resulting after a short time is filtered off and dried at 50° C. in a vacuum.

Yield: 23.0 g (71%)

Analysis: Cld: C 62.40 H 6.98 Cl 7.67 N 9.10 Fnd: C 61.70 H 7.05 Cl 7.38 N 9.25 c) N-[2-Amino-3-(4-methoxyphenyl)propyl]-cyclohexane-1,2-diamine-trihydrochloride 18.5 g (40 mmol) of $N_a$-benzyloxycarbonyl-O-methyl-tyrosine-(2-aminocyclohexyl)-amide-hydrochloride is suspended in 200 ml of methanol and mixed under nitrogen with palladium on activated carbon (10% Pd) and alternatively hydrogenated in an autoclave or under normal pressure with hydrogen. After completion of the reaction (about 2–6 hours), it is suctioned off from the catalyst and the filtrate is concentrated by evaporation. The obtained oil is suspended in 320 ml of 1M diborane/tetrahydrofuran complex solution (320 mmol) and stirred under reflux for 48 hours. Then, it is cooled in an ice bath, and the reaction is completed by adding 15 ml of methanol. It is allowed to be stirred for one hour in an ice bath and then hydrogen chloride is introduced, and the trihydrochloride of the desired amine precipitates. The precipitate is suctioned off and dried on $P_2O_5$.

Yield: 14.2 g (92%)

Analysis: Cld: C 49.68 H 7.82 Cl 27.50 N 10.86 Fnd: C 49.21 H 7.70 Cl 28.75 N 10.20

We claim:

1. Process for the production of carbon-substituted diethylenetriamines of general formula I

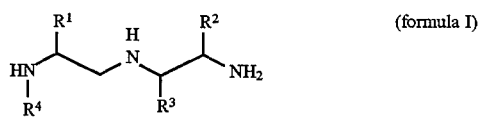 (formula I)

in which $R^1$ stands for a group $-(CH_2)_m-(C_6H_4)_q-(O)_k-(CH_6H_4)_r-(O)_r-R$ or for a group $-(CH_2)_m-(C_6H_{10})_q-(O)_k-(CH_2)_n-(C_6H_{10})_r-(O)_r-R$, in which m and n, independently of one another, mean numbers 0–5, k, l, q and r, independently of one another, mean numbers 0 or 1, R stands for a hydrogen atom, a protective group, an optionally $OR^5$-substituted $C_1-C_6$ alkyl radical or a $CH_2-COOR^5$ group, with $R^5$ meaning a hydrogen atom, a $C_1-C_6$ alkyl radical or a benzyl group, provided that a direct oxygen-oxygen bond is not allowed, $R^2$ and $R^3$ each stand for a hydrogen atom or together form a $-(CH_2)_p$-alkylene bridge, in which p means numbers 3 or 4 and $R^4$ stands for an amino protective group, characterized in that an aminoethyl alcohol, protected on nitrogen, of general formula II

 (formula II)

in which $R^1$ and $R^4$ have the indicated meanings, is reacted with methanesulfonic acid chloride, tosyl chloride or trifluoroacetic anhydride in an organic solvent, by adding a base, to the corresponding mesylate, tosylate or triflate, is then filtered and the filtrate is reacted with an ethylenediamine of general formula III

 (formula III)

in which $R^2$ and $R^3$ have the indicated meanings to the desired nitrogen-protected, carbon-substituted triamine of general formula I.

2. Process according to claim 1, wherein the group $-(CH_2)_m-(C_6H_4)_q-(O)_k-(CH_2)_n-(C_6H_4)_r-(O)_r-R$ stands for an isobutyl, benzyl, 4-ethoxybenzyl radical or a 4-methoxybenzyl radical.

3. Process according to claim 1, wherein as an amino protective group, $R^4$ is a benzyloxycarbonyl radical.

4. Process according to claim 1, wherein triethylamine is used as a base.

5. Process according to claim 1, wherein the nitrogen-protected amino alcohol of formula II is reacted with methanesulfonic acid chloride.

6. Process according to claim 1, wherein the nitrogen-protected amino alcohol of formula II is reacted with toluenesulfonic acid chloride.

* * * * *